(12) United States Patent
Lorenz et al.

(10) Patent No.: US 10,902,606 B2
(45) Date of Patent: Jan. 26, 2021

(54) HEART MODEL GUIDED CORONARY ARTERY SEGMENTATION

(71) Applicant: KONINKLIJKE PHILIPS N.V., Eindhoven (NL)

(72) Inventors: Cristian Lorenz, Hamburg (DE); Tobias Klinder, Uelzen (DE); Holger Schmitt, Luetjensee (DE); Hannes Nickisch, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 134 days.

(21) Appl. No.: 16/060,453

(22) PCT Filed: Dec. 19, 2016

(86) PCT No.: PCT/IB2016/057758
§ 371 (c)(1),
(2) Date: Jun. 8, 2018

(87) PCT Pub. No.: WO2017/109662
PCT Pub. Date: Jun. 29, 2017

(65) Prior Publication Data
US 2018/0365838 A1   Dec. 20, 2018

Related U.S. Application Data

(60) Provisional application No. 62/270,981, filed on Dec. 22, 2015.

(51) Int. Cl.
*G06T 7/149* (2017.01)
*G06T 7/11* (2017.01)
(Continued)

(52) U.S. Cl.
CPC .......... *G06T 7/149* (2017.01); *G06T 7/11* (2017.01); *G06T 7/12* (2017.01); *G16H 50/50* (2018.01);
(Continued)

(58) Field of Classification Search
CPC .. G06T 7/149; G06T 7/12; G06T 7/11; G16H 50/50
See application file for complete search history.

(56) References Cited

U.S. PATENT DOCUMENTS 8,157,742 B2   4/2012   Taylor
8,200,466 B2   6/2012   Spilker
(Continued)

FOREIGN PATENT DOCUMENTS

DE   102008014792   6/2009
WO   00/72037       11/2000
(Continued)

OTHER PUBLICATIONS

Svensson et al., "Digital Distance Transforms in 3D images using information from neighborhoods up to 5x5x5", Computer Vision and Image Understanding 88, 24-53 (2002).
(Continued)

*Primary Examiner* — Md K Talukder
(74) *Attorney, Agent, or Firm* — Larry Liberchuk

(57) ABSTRACT

A system (100) for segmenting a coronary artery vessel tree (182) of a patient heart in a three dimensional (3D) cardiac image (120) includes a coronary volume definition unit (150) and a coronary artery segmentation unit (180). The coronary volume definition unit (150) sets a spatial boundary (210, 220) from internal and external surfaces of heart tissues in the 3D cardiac image based on a fitted heart model (200). The coronary artery segmentation unit (180) segments the coronary artery vessel tree (182) in the 3D cardiac
(Continued)

image using a segmentation algorithm with a search space limited by the spatial boundary set from the internal and external surfaces of the heart tissues.

17 Claims, 3 Drawing Sheets

(51) Int. Cl.
  *G06T 7/12* (2017.01)
  *G16H 50/50* (2018.01)
  *A61B 5/026* (2006.01)

(52) U.S. Cl.
  CPC ..... *A61B 5/026* (2013.01); *G06T 2207/10076* (2013.01); *G06T 2207/10081* (2013.01); *G06T 2207/10088* (2013.01); *G06T 2207/30048* (2013.01); *G06T 2207/30101* (2013.01)

(56) References Cited

U.S. PATENT DOCUMENTS

| | | | |
|---|---|---|---|
| 8,249,815 B2 | 8/2012 | Taylor | |
| 8,867,822 B2 | 10/2014 | Oh | |
| 9,129,417 B2 | 9/2015 | Zheng | |
| 2006/0056694 A1* | 3/2006 | Rinck | G06T 7/11 382/173 |
| 2010/0125197 A1 | 5/2010 | Fishel | |
| 2010/0130878 A1 | 5/2010 | Lasso | |
| 2010/0241404 A1 | 9/2010 | Taylor | |
| 2011/0211742 A1 | 9/2011 | Bredno | |
| 2011/0307231 A1 | 12/2011 | Kirchner | |
| 2012/0022843 A1 | 1/2012 | Ionasec | |
| 2012/0041318 A1* | 2/2012 | Taylor | A61B 5/4848 600/504 |
| 2012/0041319 A1 | 2/2012 | Taylor | |
| 2012/0041320 A1 | 2/2012 | Taylor | |
| 2012/0041321 A1 | 2/2012 | Taylor | |
| 2012/0041322 A1 | 2/2012 | Taylor | |
| 2012/0041323 A1 | 2/2012 | Taylor | |
| 2012/0041324 A1 | 2/2012 | Taylor | |
| 2012/0041325 A1 | 2/2012 | Taylor | |
| 2012/0041739 A1 | 2/2012 | Taylor | |
| 2012/0053919 A1 | 3/2012 | Taylor | |
| 2012/0059246 A1 | 3/2012 | Taylor | |
| 2012/0072190 A1 | 3/2012 | Sharma | |
| 2012/0121151 A1 | 5/2012 | Bernhardt | |
| 2012/0243761 A1 | 9/2012 | Senzig | |
| 2012/0296199 A1 | 11/2012 | Kim | |
| 2013/0216110 A1* | 8/2013 | Zheng | G06T 7/66 382/128 |
| 2014/0114618 A1 | 4/2014 | Fonte | |
| 2014/0219524 A1* | 8/2014 | Takeguchi | A61B 8/5207 382/128 |
| 2018/0365838 A1* | 12/2018 | Lorenz | G16H 50/50 |
| 2019/0042834 A1* | 2/2019 | Gavino | G06T 5/002 |

FOREIGN PATENT DOCUMENTS

| | | |
|---|---|---|
| WO | 2004025572 | 3/2004 |
| WO | 200661814 | 6/2006 |
| WO | 200661815 | 6/2006 |
| WO | 2007/072363 | 6/2007 |
| WO | 201022762 | 3/2010 |
| WO | 2012063204 | 5/2012 |

OTHER PUBLICATIONS

Calvin et al. "A linear time algorithm for computing exact Euclidean distance transforms of binary images in arbitrary dimensions." IEEE Transactions on Pattern Analysis and Machine Intelligence, vol. 25, No. 2, Feb. 2003.

Buelow et al "A general framework for tree segmentation and reconstruction from medical volume data", Medical Image Computing and Computer-Assisted Intervention—MICCAI 2004 pp. 533-540.

Nickisch, et al., "Learning Patient-Specific Lumped Models for Interactive Coronary Blood Flow Simulations", Springer International Publishing Switzerland 2015.

Taylor, et al., "Computational Fluid Dynamics Applied to Cardiac Computed Tomography for Noninvasive Quantification of Fractional Flow Reserve", Journal of the American College of Cardiology, vol. 61, No. 22, 2013.

Ecabert, et al., "Automatic Model-Based Segmentation of the Heart in CT Images", IEEE Transactions on Medical Imaging, vol. 27, No. 9, Sep. 2008.

Zheng, et al., "Machine Learning Based Vesselness Measurement for Coronary Artery Segmentation in Cardiac CT Volumes", SPIE Medical Imaging, 2011.

* cited by examiner

HEART MODEL GUIDED CORONARY ARTERY SEGMENTATION

CROSS REFERENCE TO RELATED APPLICATIONS

This application is the U.S. National Phase application under 35 U.S.C. § 371 of International Application No. PCT/IB2016/057758, filed Dec. 19, 2016, published as WO 2017/109662 on Jun. 29, 2017, which claims the benefit of U.S. Provisional Patent Application No. 62/270,981 filed Dec. 22, 2015. These applications are hereby incorporated by reference herein.

FIELD OF THE INVENTION

The following generally relates to medical imaging with specific application to coronary artery segmentation.

BACKGROUND OF THE INVENTION

Accurate computation of virtual fractional flow reserve (FFR) using a digital representation of a segmented coronary artery vessel depends on the accuracy of the segmented vessel. This virtual method is non-invasive in contrast with a more conventional method using an invasive catheter based actual FFR measurement. FFR measures pressure differences across a coronary artery stenosis to determine a likelihood that a stenosis impedes oxygen delivery to the heart muscle.

Current approaches to segmentation of the coronary artery use a three dimensional (3D) volume image of the cardiac region, such as generated from a computed tomography (CT) image, or a magnetic resonance (MR) image. The modalities provide a resolution sufficient to identify at least the larger diameter portions of the coronary artery tree which includes the coronary artery and the vessels that branch from the coronary artery and supply oxygen to the tissues of the heart. Due to limits on resolution and artifacts, such as motion artifacts, the boundaries of vessels are not always clearly delineated, e.g. blurred, indistinct, etc. These imaging aspects in combination with variability in anatomical structure of the coronary artery tree from subjects make accurate representations of the coronary vessel tree difficult.

The current approaches use various algorithms to define a coronary vessel tree, such as seed growing algorithms with parameters that are difficult to control. For example, the algorithms generally use a comparison of adjacent or neighboring voxels with the current growing region to determine whether to add the compared voxel to the current growing region. The algorithms rely on image properties, such as a change in intensity to make the determination of whether or not to add the compared voxel, e.g. if difference is less than a threshold amount determined by a parameter, then add otherwise do not add.

One of the problems encountered in conventional approaches to segmentation of the coronary artery tree is leakage of the segmentation into nearby structures. For example, in region growing algorithms, this typically occurs where the boundaries are blurred or less distinct, and the growing algorithm adds voxels of nearby structures, such as the heart chambers, myocardium, or pulmonary artery, into the current growing region. Some algorithms try to control for this leakage based on adjustments of parameters. The parameters control the intensity thresholds or measured intensities in combinations of voxels, which becomes computationally expensive, e.g. long run-times, and can miss smaller branches of the vessel tree, such as those close to image resolution, e.g. only a few millimeters in diameter.

Heart models are known in the art, which are typically used for heart segmentation or heart motion correction. For example, a digital representation of a heart can include tissues of the heart represented as triangular meshes. The model is fit to the imaged heart, and motion correction is determined from matching the model at different phases to the image heart. However, the heart models typically include (if at all) only the large diameter vessels, and do not include entire vessel trees.

SUMMARY OF THE INVENTION

Aspects described herein address the above-referenced problems and others.

The following describes a method and system for a heart model guided coronary artery segmentation. The heart model is fit to internal and external surfaces of a heart in image data and the fitted heart model is used to provide spatial limitations for the coronary artery segmentation. A fitted coronary artery probability map can be used to guide the segmentation.

In one aspect, a system for segmenting a coronary artery vessel tree of a patient heart in a three dimensional (3D) cardiac image includes a coronary volume definition unit and a coronary artery segmentation unit. The coronary volume definition unit sets a spatial boundary from internal and external surfaces of heart tissues in the 3D cardiac image based on a fitted heart model. The coronary artery segmentation unit segments the coronary artery vessel tree in the 3D cardiac image using a segmentation algorithm with a search space limited by the spatial boundary set from the internal and external surfaces of the heart tissues.

In another aspect, a method of segmenting a coronary artery vessel tree of a patient heart in a three dimensional (3D) cardiac image includes setting a spatial boundary from internal and external surfaces of heart tissues in the 3D cardiac image based on a fitted heart model. The coronary artery vessel tree in the 3D cardiac image is segmented using a segmentation algorithm with a search space limited by the spatial boundary set from the internal and external surfaces of the heart tissues.

In another aspect, a system for segmenting a coronary artery vessel tree of a patient heart in a medical image includes one or more processors configured to segment the coronary artery vessel tree in the image using a segmentation algorithm with a search space limited by a spatial boundary set from internal and external surfaces of heart tissues in the image using a fitted heart model.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
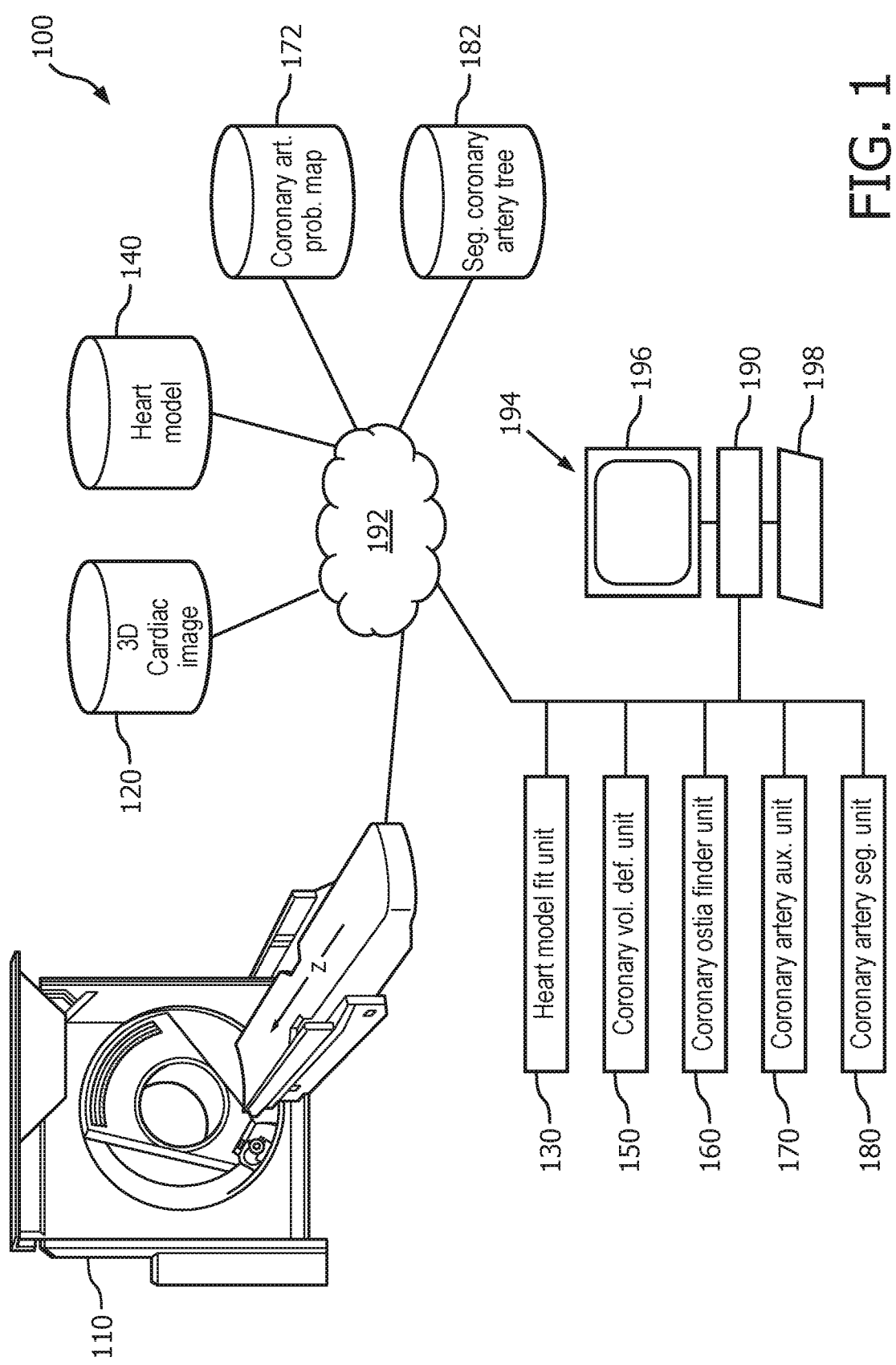
FIG. 1 schematically illustrates an embodiment of a heart model guided coronary artery segmentation system.

Initially referring to FIG. 1, a heart model guided coronary artery segmentation system 100 is schematically illustrated. A medical imaging device 110, such as a CT scanner, a MR scanner, combinations and the like, generates a three dimensional (3D) volumetric cardiac image 120. The 3D cardiac image 120 is of sufficient spatial resolution to show the coronary artery, such as a millimeter or better. The generated image can include the use of an administered contrast agent, which contrasts the coronary artery lumen. The generated 3D cardiac image 120 can be prospectively or retrospectively gated to reduce motion artifacts. The 3D cardiac image 120 can include the heart and surrounding tissues or portions of the heart and surrounding tissues.

A heart model fit unit 130 fits an anatomical heart model 140 known in art to the heart in the 3D cardiac image. The heart model 140 is a digital spatial representation of the tissues of the heart. The heart model can include labeled anatomical points or regions. The heart model fit unit 130 elastically fits the heart model to the imaged heart, e.g. individualizes the heart model to a specific patient. For example, the surfaces of the tissues can be represented as triangular meshes. The fit can be based on matching of anatomical points or regions in heart model 140 to anatomical points in the heart in the 3D cardiac image 120, such as positions of valves, apexes, septum, chordae tendineae, etc. Points or regions of the elastic mesh can be anchored at the matched anatomical points or regions and the elastic mesh can be adjusted to match the surface of the corresponding tissue.

With the surface of the patient heart fitted with the heart model, a coronary volume definition unit 150 sets a spatial boundary from the surface of the heart tissues. The search space includes myocardial tissues between the surfaces of the heart tissues along with the arterial feeds disposed in that spatial region. In some instances this ensures that arterial flow that goes deeply into the heart tissues is included in the search space. A first bounding distance $d_1$ outside heart is set for external heart surfaces outside, which excludes tissues, such as the pulmonary vasculature. A second bounding distance $d_2$ is set for surfaces inside heart, which excludes volumes such as heart chambers. For example, the first distance can extend externally 1.5 centimeters (cm) perpendicular to the external heart surface and the second distance extends internally 1.0 cm perpendicular to the internal heart surfaces. Another example uses 3.0 cm and 2.0 cm as the external and internal distances. In another example, the distances are the same externally and internally of 1.5 cm or 3.0 cm. Other distances are contemplated. The bounding distance inside and outside of the organ can be different or the same. In one embodiment, the bounding distances can be graduated according to a distance along the heart surface decreasing in distance toward the ventricles. In one embodiment, the graduate distances include a function of a spatial distance from a start of the coronary artery along the heart surface. For example, as the artery decreases in diameter, such as by branching, the search space can be moved closer to the heart surface.

A coronary ostia finder unit 160 finds initial seed points from left and right coronary artery ostium based on the fitted heart model. For example, the coronary ostia finder unit 160 uses marked triangles from the mesh model to begin search through ascending aorta model wall identifying a transition in contrast from medium to high intensity corresponding to the left and right coronary ostia.

A coronary artery auxiliary unit 170 generates and maintains the coronary artery probability map 172, which includes a probability that each voxel is part of the coronary artery vessel tree. Based in part on the larger vessels of the fitted heart model, and the probability map 172 can generated for the coronary artery and branches based on a distribution of the vessel tree across a sample population and matched to or fused with the heart model. For example, a sample of segmented coronary arteries from a healthy patient population are deformably registered to the heart model, and a probability computed as a function of a frequency of occurrences of the segmented coronary arteries in each voxel. The probabilities according to each voxel or spatial location according to the heart model form the probability map 172. In one embodiment, the probability map can be stored as part of the heart model, in which each surface element stores the probabilities for a set of voxels surrounding the surface element. As the heart model is elastically fitted, the probability map is elastically fitted as well. In some embodiments, the fitted probability map 172 can be used to exclude loops in the segmentation, such as at the vessel segment level. A loop occurs when a vessel appears to feed itself. In some embodiments, the fitted probability map 172 can be used with thresholds values, such as in bifurcation of branches. For example, arteries branch within angles of 0-70 degrees, which can be used as a threshold to limit a local search space of neighboring voxels.

The coronary artery segmentation unit 180 segments the coronary artery vessel tree 182 with a segmentation algorithm bounded by the spatial boundaries determined by the coronary volume definition unit 150. Suitable algorithms can include tree segmentation frame works or distance map approaches, such as, T. Buelow et al "A general framework for tree segmentation and reconstruction from medical volume data" using a fast marching as region expansion with measures including vessel voxels, vessel segments, and a whole vessel tree. Another example, is a method described by T. Klinder et al. "Robust Peripheral Airway Segmentation" that can be adapted to arterial vessels, and uses a filter based vessel candidate detection with segment connection functionality. Examples of distance map approaches can include S. Svensson et al. "Digital Distance Transforms in 3D images using information from neighborhoods up to 5×5×5" and R. Calvin et al. "A linear time algorithm for computing exact Euclidean distance transforms of binary images in arbitrary dimensions." Other algorithms are contemplated. In some instances, the spatial boundary reduces segmentation run-time by decreasing search space. In some instances, segmentation robustness is increased by eliminating structures typically causing leakage, such as heart chambers, and pulmonary vasculature. Acceptance criteria for inclusion in the segmented vessel tree 182 can include voxel based acceptance, such as a distance measure, a probability and/or a directional flow, a vessel-segment acceptance, such as a probability of a next branch, and/or a whole vessel tree level acceptance.

The heart model fit unit 130, the coronary volume definition unit 150, the coronary ostia finder unit 160, the coronary artery auxiliary unit 170, and the coronary artery segmentation unit 180 comprise one or more configured processors 190, e.g., a microprocessor, a central processing unit, a digital processor, and the like. The one or more configured processors 190 are configured to execute at least one computer readable instruction stored in a computer readable storage medium, which excludes transitory medium and includes physical memory and/or other non-transitory medium to perform the techniques described herein. The one or more processors 190 may also execute one or more computer readable instructions carried by a carrier wave, a signal or other transitory medium. The one or more processors 190 can include local memory and/or distributed memory. The one or more processors 190 can include hardware/software for wired and/or wireless communications over a network 192. For example, the lines indicate communications paths between the various components which can be wired or wireless. The one or more processors 190 can comprise the computing device 194, such as a desktop, a laptop, a body worn device, a smartphone, a tablet, and/or cooperative/distributed computing devices including one or more configured servers (not shown). The computing device 194 can include a display device 196, which can display the segmented vessel tree 182 or computations made from the segmented vessel tree 182, such as FFR. The computing device 194 can include one or more input devices 198 which receive commands, such as identifying the 3D cardiac image 120, confirming seed points by the coronary ostia finder unit 160, displaying the coronary probability map 172, and/or segmenting the coronary artery vessel tree 182.

The 3D cardiac image 120, the heart model 140, the segmented coronary artery tree 182 are represented as digital data sets stored on an electronic storage medium or computer memory. The 3D cardiac image 120 can include a Digital Imaging and Communications in Medicine (DICOM) format or other suitable image format.

Figure 2:
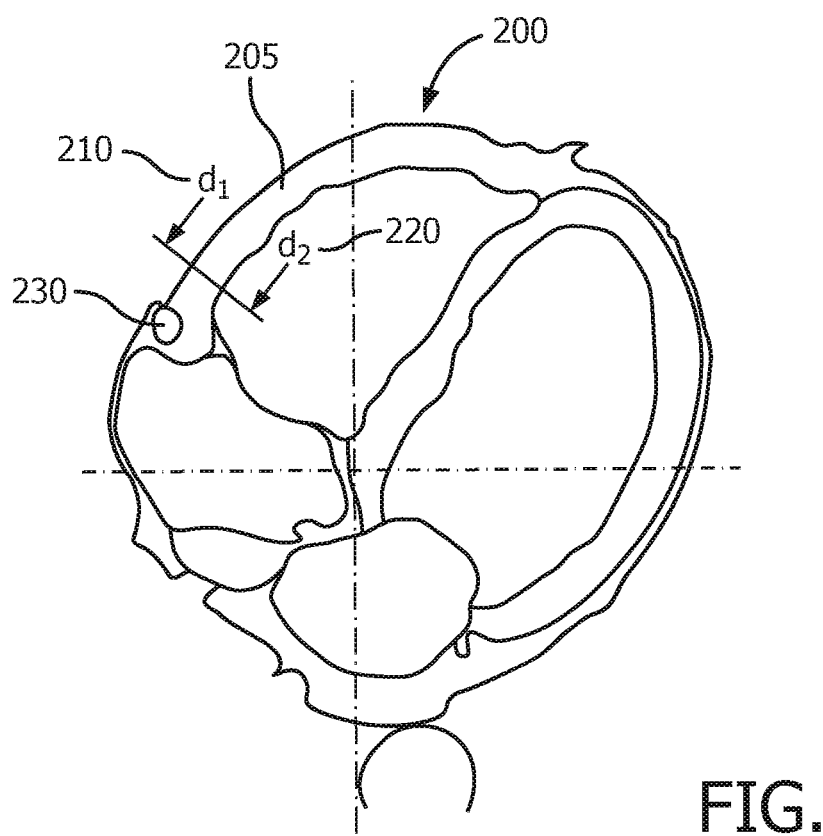
FIG. 2 illustrate an exemplary cross section of a heart model fitted to internal and external heart surfaces in a patient image and a spatial boundary determination.

With reference to FIG. 2, an exemplary cross section of a fitted heart model 200 fitted to internal and external surfaces of a heart from the 3D cardiac image 120 and spatial boundary determination is illustrated. Tissues, such as myocardial tissues 205, represented in the fitted heart model 200 are illustrated superimposed over the tissues represented in the 3D cardiac image 120. From the exterior surface of the fitted heart model 200, the first boundary 210, $d_1$, is determined. The first boundary is defined as a surface of distance $d_1$ determined by orthogonal projections from the mesh surface of the fitted heart model 200. Tissues external to the first boundary 210 are excluded from the search space of the segmentation algorithm.

From the interior surface of the fitted heart model 200, the second boundary 220, $d_2$ is determined. Tissues enclosed by a surface defined by the second boundary 220 are also excluded from the search space of the segmentation algorithm, e.g. chamber volumes. The two boundary determinations are made with distances such that search space includes the coronary artery vessel tree including myocardial tissues between the external surface and internal surface with their associated arterial supply. In some embodiments, the boundary determinations excludes tissues identified from the fitted heart model 200 that have a low probability of including the coronary artery vessel tree based on the fitted probability map.

From the fitted model 200, a lumen 230 of the coronary artery can be located and initial seed points for the segmentation algorithm determined, such as the ostia of the left and right coronary artery. The ostia can be automatically identified and confirmed visually by a healthcare practitioner.

Figure 3:
FIG. 3 illustrates an exemplary coronary artery probability map.

With reference to FIG. 3, an exemplary coronary artery probability map 172 is illustrated. The probability map 172 is illustrated visually as a two dimensional (2D) representation of the 3D map with 2D pixels darkened according to corresponding probability, e.g. darker pixels with higher probability of belonging to coronary artery vessel tree. The probabilities of the coronary artery probability map 172 are represented corresponding to spatially located 3D voxels.

The coronary artery probability map 172 can include probabilities for conflicting structures, such as the coronary venous system. The coronary artery probability map 172 can include distance values, such as typical distances values between a nearest artery and an endocardial surface, such as represented with a triangle of the fitted mesh model. The coronary artery probability map 172 can include a directional weighted probabilities based on arterial flow, e.g. higher probability of adjacent voxels along centerline of lumen with decreasing probability as angle increases away from the centerline.

Figure 4:
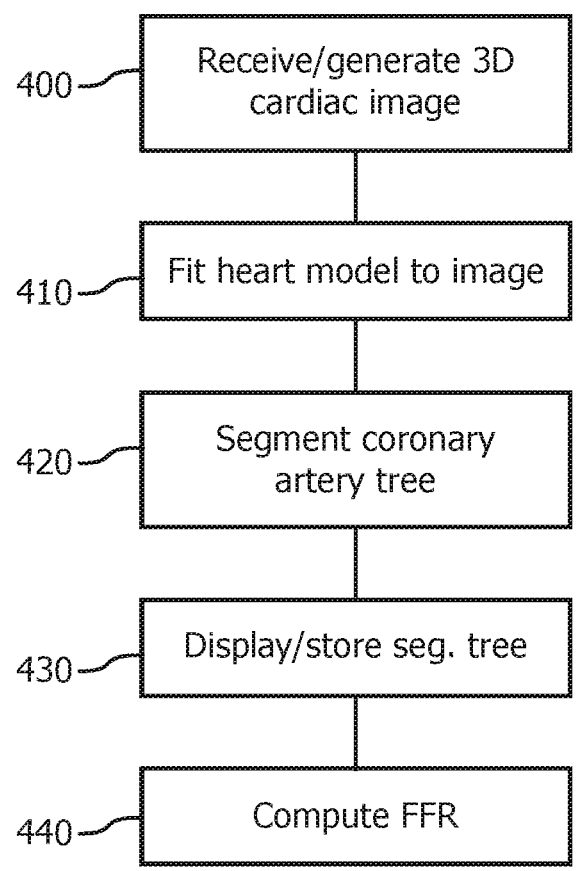
FIG. 4 flowcharts an embodiment of a method of segmenting a coronary artery vessel tree based on the fitted heart model.

With reference to FIG. 4, an embodiment of a method of segmenting a coronary artery vessel tree based on the fitted heart model is flowcharted. At 400, the 3D cardiac image 120 is received. The 3D cardiac image 120 can be received from a storage subsystem, such as a Picture Archiving and Communication System (PACS), departmental Radiology Information System (RIS), Electronic Medical Record (EMR), and the like. The 3D cardiac image 120 can be generated by the medical imaging device 110 and received directly from the medical imaging device 110.

At 410, the heart model 140 is fitted to the heart in the 3D cardiac image 120. The fitted heart model 200 includes defined tissue surfaces that are fitted to the tissue surfaces of the heart in the 3D cardiac image 120. The first boundary 210 and the second boundary 220 are determined from the fitted heart model 200. Surfaces of the boundaries limit the search space. The coronary artery probability map 172 is fit based on the fitted heart model 200 and included in the search space. The coronary artery probability map 172 is constructed from a sampling of segmented coronary artery vessel trees deformably registered to the heart model 140. Probabilities can be computed from the sampling distribution. The coronary artery probability map 172 can include distance measures to the nearest artery, a directional indicator of the arterial flow and/or a branching threshold.

The coronary artery vessel tree 182 is segmented at 420. The segmentation can include identifying seed points with a search for the seeds points based on the fitted heart model 200. The segmentation can include revising or updating the probability map 172 based on acceptance level at the voxel, segment, or whole vessel tree. The segmentation includes spatially limiting the search space to the volume between the surfaces defined by the first boundary 210 and the second boundary 220. The segmented coronary artery vessel tree 182 includes a digital representation that for each spatially located voxel defines whether a voxel is included in the vessel lumen. In one embodiment, the digital representation can include stenosis, such as calcium, plaque, etc.

At 430, the coronary artery vessel tree 182 can be stored in a computer memory and/or displayed on the display device 196. The coronary artery vessel tree 182 or portions thereof can be displayed as 2D projections. The projections can include interior navigation, different perspectives, color contrast, and the like. The projections can include measurements, such as diameters, which are contrasted in the display. The projections can include visual contrasts of stenosis and/or materials, such as plaque, calcium, etc.

At 440, a fractional flow reserve value (FFR) can be computed based on the segmented coronary artery vessel tree 182. The FFR can be used to identify and rate stenosis in the vessel tree 182.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system, comprising:
    coronary volume definition processor circuitry configured to set a spatial boundary from internal and external surfaces of heart tissues in the 3D cardiac image based on a fitted heart model;
    coronary artery segmentation processor circuitry configured to segment a coronary artery vessel tree of a patient heart in a three dimensional (3D) cardiac image using a segmentation algorithm with a search space limited by the spatial boundary set from the internal and external surfaces of the heart tissues; and
    coronary artery auxiliary processor circuitry configured to construct a coronary artery probability map from a sampling of segmented coronary arteries deformably fit to a heart model of the fitted heart model, and
    wherein the coronary artery probability map includes a probability based on a directional arterial flow that a corresponding spatially located voxel is included in the coronary artery vessel tree.

2. The system according to claim 1, wherein the spatial boundary includes a first boundary of a first distance from external heart surfaces and excludes from segmentation tissues external to the first distance and a second boundary of a second distance from internal heart surfaces and excludes from segmentation tissues enclosed by the second distance.

3. The system according to claim 1, wherein the coronary artery probability map is constructed from a sampling of segmented coronary arteries deformably fit to a heart model of the fitted heart model.

4. The system according to claim 1, further comprising:
    coronary ostia finder processor circuitry configured to identify initial see points for the segmentation algorithm located based on predetermined points identified based on the fitted heart model.

5. The system according to claim 2, wherein the first boundary distance and the second boundary distance are different.

6. The system according to claim 1, wherein the external surfaces and the internal surfaces are different surfaces.

7. The system according to claim 2, wherein the first boundary distance is graduated and decreasing toward an apex of the patient heart.

8. The system according to claim 1, wherein the coronary artery probability map includes a probability that a corresponding spatially located voxel is included in the coronary artery vessel tree.

9. The system according to claim 1, wherein the coronary artery segmentation processor circuitry is configured to cause the spatial boundary to reduce a segmentation run-time by decreasing the search space.

10. A method, comprising:
    setting a spatial boundary from internal and external surfaces of heart tissues in the 3D cardiac image based on a fitted heart model; and
    segmenting a coronary artery vessel tree of a patient heart in a three dimensional (3D) cardiac image using a segmentation algorithm with a search space limited by the spatial boundary set from the internal and external surfaces of the heart tissues,
    wherein the setting includes:
    constructing the coronary artery probability map from a sampling segmented coronary arteries deformably fit to a hear model of the fitted heart model, and
    wherein the coronary artery probability map includes a probability based on a directional arterial flow that a corresponding spatially located voxel is included in the coronary artery vessel tree.

11. The method according to claim 10, wherein the spatial boundary includes a first boundary of a first distance from external heart surfaces and excludes from segmentation tissues external to the first distance and a second boundary of a second distance from the internal heart surfaces and excludes from segmentation tissues enclosed by the second distance.

12. The method according to claim 10, wherein the segmenting includes fitting a coronary artery probability map based on the fitted heart model; and
    wherein the segmentation algorithm uses the probability map to guide segmentation based on the probability map.

13. The method according to claim 10, wherein the segmenting includes identifying initial seed points for the segmentation algorithm located based on predetermined points identified based on the fitted heart model.

14. The method according to claim 10, wherein the first boundary distance and the second boundary distance are different.

15. The method according to claim 10, wherein the internal and external surfaces are different surfaces.

16. The method according to claim 10, wherein the coronary artery probability map includes a probability that a corresponding spatially located voxel is included in the coronary artery vessel tree.

17. The method according to claim 10, wherein the spatial boundary reduces a segmentation run-time by decreasing the search space.

* * * * *